United States Patent
Hajicek et al.

(10) Patent No.: US 7,638,649 B2
(45) Date of Patent: Dec. 29, 2009

(54) METHOD OF PREPARATION OF (R)-(−)-5-(2-AMINOPROPYL)-2-METHOXY BENZENESULFONAMIDE

(75) Inventors: Josef Hajicek, Praha (CZ); Marketa Slavikova, Libcice nad Vltavou (CZ)

(73) Assignee: Zentiva, k.s., Praha (CZ)

( * ) Notice: Subject to any disclaimer, the term of this patent is extended or adjusted under 35 U.S.C. 154(b) by 444 days.

(21) Appl. No.: 10/588,515

(22) PCT Filed: Feb. 3, 2005

(86) PCT No.: PCT/CZ2005/000010

§ 371 (c)(1),
(2), (4) Date: Jan. 11, 2007

(87) PCT Pub. No.: WO2005/075415

PCT Pub. Date: Aug. 18, 2005

(65) Prior Publication Data

US 2008/0319225 A1   Dec. 25, 2008

(30) Foreign Application Priority Data

Feb. 5, 2004   (CZ) ............... PV 2004-197

(51) Int. Cl.
*C07C 311/39* (2006.01)
(52) U.S. Cl. ...................................... 564/69
(58) Field of Classification Search ............ 564/86
See application file for complete search history.

(56) References Cited

FOREIGN PATENT DOCUMENTS

| AT | 397 960 | 8/1994 |
|---|---|---|
| EP | 0 257 787 | 3/1988 |
| WO | 02 068382 | 9/2002 |

*Primary Examiner*—Peter G O'Sullivan
(74) *Attorney, Agent, or Firm*—Oblon, Spivak, McClelland, Maier & Neustadt, P.C.

(57) ABSTRACT

A method of preparation of (R)-(−)-5-(2-aminopropyl)-2-methoxybenzenesulfonamide of formula I and its use for production tamsulosin. A protective group is introduced to N-[(1R)-2(4-methoxyphenyl)-1-methylethyl]-N-[(1R)-1-phenylethyl)]amine and the resulting amide of formula IX is chlorosulfonated and the resulting sulfochloride is converted to a sulfonamide of formula X, from which the compound of formula I is obtained by hydrogenation.

12 Claims, No Drawings

METHOD OF PREPARATION OF (R)-(−)-5-(2-AMINOPROPYL)-2-METHOXY BENZENESULFONAMIDE

TECHNICAL FIELD

The invention concerns an improved method of preparation of (R)-(−)-5-(2-aminopropyl)-2-methoxybenzenesulfonamide of formula I

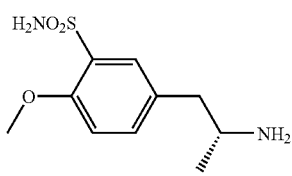

which is an important intermediate product for the preparation of medical product (R)-(−)-5-[2-[2-(2-ethoxyphenoxy) ethylamino]propyl]-2-methoxybenzenesulfonamide known under the international non-proprietary name tamsulosin of formula II

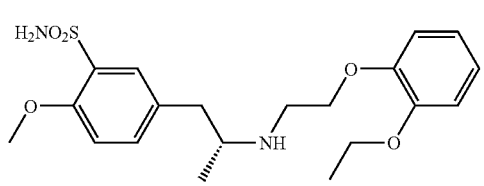

BACKGROUND ART

Substance II is known as a selective blocker of $\alpha_{1C}$ receptors, which allows for its use for treating problems with retention of urine in connection with hyperplastic prostate without influencing blood pressure. This property differentiates the substance from a number of other blockers of $\alpha_{1C}$ receptors that do not act selectively and, therefore, exhibit side effects in the form of hypotension connected with various unpleasant conditions of the patient (for example EP 710 486).

A mixture of the (R) and (S) enantiomers of 5-[2-[2-(2-ethoxyphenoxy)ethylamino]propyl]-2-methoxybenzenesulfonamide (thereinafter racemic tamsulosin) was described in patent EP 34 432. The method of preparation of the group of sulfamoyl-phenylethylamine derivatives claimed in the patent consisted in reductive amination (or amination with subsequent reduction) of ketones of type III

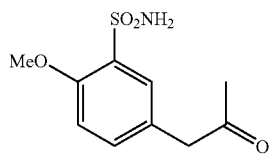

The group of substances described in patent EP 34 432 was characterized by the property to block α adrenergic receptors, which makes them suitable agents for treatment of a number of diseases, especially hypertension, congestive heart failure or problems connected with urinary tract.

Later, it turned out that the above mentioned substance II, especially the (R)-enantiomer, exhibits selective effect during treatment of problems connected with hyperplastic prostate without influencing blood pressure or heart action (Honda K. and Nakagawa C: Alpha-1-adrenoreceptor antagonist effect of optical isomers YM-12617 in rabbit lower urinary tract and prostate—J. Pharm Exp. Ther. 239, 512, (1986)).

This led to attempts at effective synthesis of optically active substance II.

In the Austrian patent AT 397960, the synthesis of (R)-tamsulosin (II) is solved by reaction of optically active amine of formula I

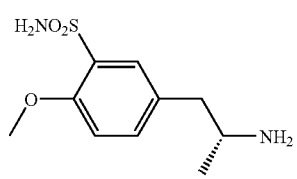

with brominated ether of formula IV

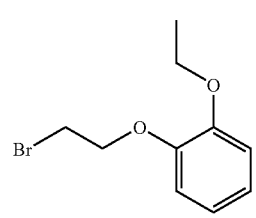

The synthesis turned out to be very advantageous if the starting amine I was prepared according to the method described in patent EP 257785, or divisional EP 380144.

The patents describe the path indicated in the following scheme:

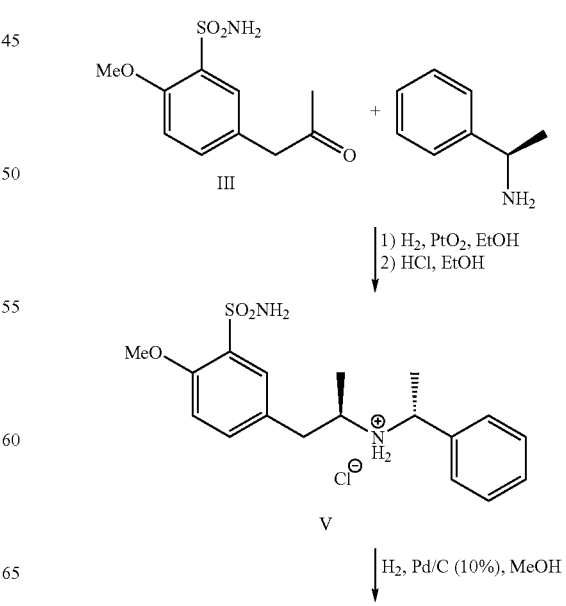

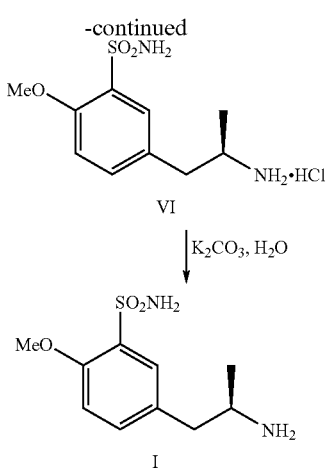

Reaction of ketone III with (R)-α-methylbenzylamine in a reductive environment under catalysis of PtO₂ results in optically active (R,R)-diastereoisomer V with high optical purity (around 92%). This intermediate product is further re-crystallized to obtain high optical purity and converted, by hydrogenolysis, to optically active (R)-hydrochloride VI. The latter is converted to the (R)-amine of formula I itself by action of a base.

However, a reproduction of this procedure has shown that the yield of R amine I ranges between 10 and 15% and that of resulting tamsulosin II even only about 4 to 5% of the theory. The yield of the last stage of the synthesis, i.e. preparation of the substance II from the substance I, was significantly improved according to patent CZ 291802. However, there is still the problem of very low yield of the important intermediate I.

However, surprisingly, such a method has now been found out that can produce even higher than twofold yield.

DISCLOSURE OF INVENTION

The starting substance for preparation of the amine of formula I is methylbenzylketone (VII), from which N-[(1R)-2-(4-methoxyphenyl)-1-methylethyl]-N-[(1R)-1-phenylethyl)]amine hydrochloride of formula VIII is obtained via reductive amination

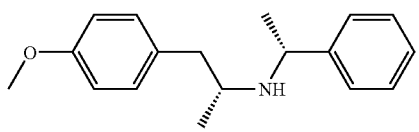

Hydrogenation takes place under normal pressure for about 12 hours with addition of a catalyst in the amount of 0.6 g/1 mol methylbenzylketone, which is about 60% of the consumption according to patent EP 257787. Considering that the cost of catalyst makes a significant part of raw-material costs, it is a sizable saving. Also avoided is multiple purifying in acetone and the water-acetone mixture; in most cases, it is sufficient to repeat purifying in acetone only 1 to 3 times. Decreasing the requirements for optical purity from the limit of 0.2% to the tolerable content of 0.4% of the R,S-enantiomer does not have any impact on high optical purity of the final product of formula II. The yields of the reaction are about 50%. Introduction of the protective group A, wherein A can be an acyl having 2 to 8 carbons, such as for example acetyl, propionyl, hexanoyl or benzoyl, by reaction with anhydrous acid, halide or anhydride of the respective acid, leads to the amide of formula IX

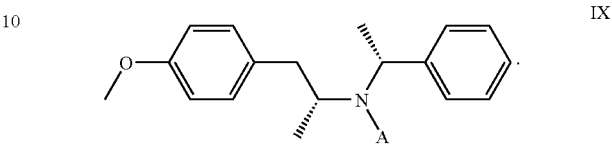

After N-acetylation with acetanhydride, N-[(1R)-2-(4-methoxyphenyl)-1-methylethyl]-N-[(1R)-1-phenylethyl]acetamide is thus obtained. The reaction runs for 4 to 6 hours at a temperature of 60 to 70° C. in high yields about 100%.

The amide of formula IX is then chlorosulfonated and the resulting sulfochloride is converted to a sulfonamide. The reaction with chlorosulfonic acid proceeds preferably in dichloromethane with cooling to −30 to +30° C. and it is advantageous if the reaction mixture is decomposed by pouring into a mixture of ice and 25% aqueous solution of ammonia. This procedure yields directly N-{(1R)-2-[3-(aminosulfonyl)-4-methoxyphenyl]-1-methylethyl}-N-[(1R)-1-phenylethyl]acetamide of formula X

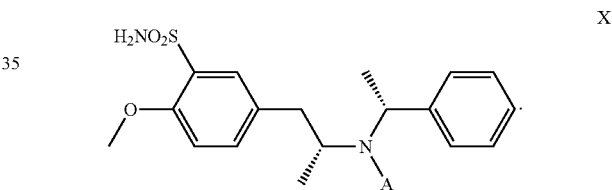

Isolation of one intermediate is thus avoided, as well as using another solvent (tetrahydrofuran) in the synthesis. The reaction has surprisingly high yields of up to 96%.

Hydrogenation on palladium in acetic acid with addition of diluted hydrochloric acid at a temperature of 80 to 85° C. and the pressure of 2 MPa results in splitting off ethylbenzene, yielding N-{(1R)-2-[3-(aminosulfonyl)-4-methoxyphenyl]-1-methylethyl}acetamide (XI). A significantly cheaper and safer catalyst —3% Pd/C with a 50% water content was used in the hydrogenation in an amount of ⅒ of the weight of the entering substance of formula X The yields of the reaction come close to 100%.

Refluxing in a 5% aqueous solution of HCl results in deacetylation of the intermediate (XI), addition of a carbonate precipitates (R)-(−)-5-(2-aminopropyl)-2-methoxybenzensulfonamide of formula I, which is re-crystallized from water. The reaction yields after crystallization are about 80%.

EXAMPLES

In the experimental part, all the ¹H-NMR data are measured using the instrument BRUKER 250-DPX (250.13 and 62.9 MHz), δ in ppm; J in Hz).

Example 1

Preparation of N-[(1R)-2-(4-methoxyphenyl)-1-methylethyl]-N-[(1R)-1-phenylethyl)]amine hydrochloride VIII 4-Methoxybenzylmethylketone (VII, 43.2 g), R(+)-methylbenzylamine (32.0 g) and catalyst $PtO_2$ (0.16 g) are weighed into a 2-l flask and methanol (1000 ml) is added. Hydrogenation is carried out until the reaction stops, for ca 12 hours at 60° C.

After the reaction is complete, the catalyst is filtered off. The filtrate is evaporated and 300 ml of ethanol are added to the yellow oil (69.47 g); a yellow solution is formed. During cooling in a water bath 50 ml of HCl/EtOH is added dropwise within 30 min; the solution gradually turns red. The reaction mixture is stirred at lab temperature for 1 hour. The precipitated crystals are sucked off and washed with 50 ml of ethanol. The precipitated crystals obtained in two fractions are refluxed in 500 ml of acetone for 1 hour. After cooling, the suspension is stirred for 2 hours under cooling with water, the precipitated crystals are sucked off and washed with 50 ml of acetone.

The yield is 48.18 g (59.9%). Analysis for GC chemical and optical purity is required and the content of the R,S-diastereoisomer must be bellow 0.4%. If the content is higher purification in acetone is repeated.

$^1$H NMR: δ 1.41 (d, J=6.5, 3H, $CH_2CH(CH_3)$); 1.95 (d, J=6.8, 3H, $PhCH(CH_3)$); 2.81(dd, J=10.0, J=12.9, 1H, $CH_2$); 3.00(bm, 1H, $CH_2CH(CH_3)$); 3.37(dd, J=4.3, J=13.0, 1H, $CH_2$); 3.76(s, 3H, $CH_3O$); 4.37(bm, 1H, $PhCH(CH_3)$); 6.78(m, 2H, $CH_{arom}$); 6.93(m, 2H, $CH_{arom}$); 7.45(m, 3H, $CH_{arom}$); 7.69(m, 2H, $CH_{arom}$); 9.80(b, $NH$, $HCl$); 10.26(b, $NH$, $HCl$).($CD_3OD$, 30° C.)

Example 2

Preparation of N-[(1R)-2-(4-methoxyphenyl)-1-methylethyl]-N-[(1R)-1-phenylethyl]acetamide IX Intermediate VIII (48 g) is weighed into a 1-l flask, ethylacetate (450 ml) is added and a 10 w.-% aqueous solution of NaOH (120 ml) is added dropwise to the resulting suspension under stirring and moderate cooling with water to lab temperature. Undissolved crystals slowly turn into a yellow solution and the reaction mixture is stirred at lab temperature for 0.5 h. The organic phase is separated, the water phase is shaken out with 1×100 ml ethylacetate and the combined organic fractions are evaporated.

Acetanhydride (200 ml) is added to the evaporation residue of the base and stirring is continued under a reflux condenser with calcium-chloride tube at 60 to 70° C. for 4 to 6 hours. Presence of the starting compound is controlled by TLC and after the reaction is complete, the reaction mixture is evaporated. A saturated solution of sodium hydrogencarbonate (100 ml) is added dropwise to the evaporation residue under stirring and cooling with water. The reaction mixture is extracted with ethylacetate (200 ml), the organic phase is separated and the aqueous layer is extracted with 1×100 ml ethylacetate. The combined organic fractions are extracted with 1×50 ml of brine and evaporated. The yield is 53.1 g (~100%).

$^1$H NMR: δ 1.27 (d, J=6.2, 3H, $CH_2CH(CH_3)$); 1.59(d, J=7.0, 3H, $PhCH(CH_3)$); 1.82(b, 1H, $CH_2$); 2.28(s, 3H, $COCH_3$); 2.31(bm, 1H, $CH_2$); 3.13(bm, 1H, $CH_2CH(CH_3)$); 3.72 (s, 3H, $CH_3O$); 5.08(m, 1H, $PhCH(CH_3)$); 6.42(m, 2H, $CH_{arom}$); 6.63(m, 2H, $CH_{arom}$); 7.38(m, 5H, $CH_{arom}$).($CDCl_3$, 30° C.)

Example 3

Preparation of N-{(1R)-2-[3-(aminosulfonyl)-4-methoxyphenyl]-1-methylethyl}-N-[(1R)-1-phenylethyl]acetamide X Dichloromethane (50 ml) is added to the evaporation residue of intermediate IX (25.39 g), stirred up and cooled to −5 to −10° C. Chlorosulfonic acid (55 ml) is slowly added dropwise under cooling, so that the temperature of the reaction mixture rises maximally to +5° C. Addition is made for 45 min and then the reaction mixture is stirred at 0 to 10° C. for 1 hour. The reaction mixture is slowly poured, under stirring and cooling, into the cooled mixture of 25% aqueous solution of ammonia (210 ml) and ice (210 g). After decomposition is complete, ethylacetate (420 ml) is added and the reaction mixture is stirred for 5 min until the precipitated crystals dissolve and let to sit at lab temperature for max 8 hours. After the reaction is complete, the organic fraction is separated, the aqueous layer is shaken with 1×210 ml ethylacetate. The combined organic fractions are evaporated. The yield is 28.82 g (90.6%).

$^1$H NMR: δ 1.26(d, J=6.5, 3H, $CH_2CH(CH_3)$); 1.58(d, J=6.9, 3H, $PhCH(CH_3)$); 1.80(b, 1H, $CH_2$); 2.30(s, 3H, $COCH_3$); 2.32(bm, 1H, $CH_2$); 3.13(bm, 1H, $CH_2CH(CH_3)$); 3.93 (s, 3H, $CH_3O$); 5.11(bm, 1H, $PhCH(CH_3)$); 6.77(m, 2H, $CH_{arom}$); 7.02(bs, 1H, $CH_{arom}$); 7.37(m, 5H, $CH_{arom}$).($CDCl_3$, 30° C.)

Example 4

Preparation of N-{(1R)-2-[3-(aminosulfonyl)-4-methoxyphenyl]-1-methylethyl}acetamide XI Intermediate X (3 g) is dissolved in acetic acid (160 ml), diluted HCl 1:1 (10 ml) and 3% Pd/C with 50% water content (0.3 g) are added. Hydrogenation runs at 80 to 85° C. and pressure of 2 MPa for 10 to 15 hours. After hydrogenation is complete, the solution is filtered and evaporated. The yield is 2.55 g (~100%).

$^1$H NMR: δ 1.10(d, J=6.6, 3H, $CH(CH_3)$); 1.87(s, 3H, $COCH_3$); 2.71(d, J=6.9, 2H, $CH_2$); 3.30(b, $NH_2$); 3.95(s, 3H, $CH_3O$); 4.05(m, 1H, $CH(CH_3)$); 7.11(d, J=8.5, $CH_{arom}$); 7.40 (dd, J=8.6, J=2.4, 1H, $CH_{arom}$); 7.68(d, J=2.2, 1H, $CH_{arom}$); 7.96(bd, $NH$). ($CD_3OD$, 30° C.

Example 5

Preparation of (R)-(−)-5-(2-aminopropyl)-2-methoxybenzenesulfonamide I

Intermediate XI (10.5 g) is boiled in 5% HCl (250 ml) under a reflux condenser for 16 to 18 h. The course of the reaction is controlled with TLC detecting the starting substance. After the reaction is complete, the reaction mixture is concentrated to about ⅓ of its volume, then, a saturated solution of sodium carbonate (50 ml) is slowly added dropwise under stirring. After the addition, pH~10 is controlled and the reaction mixture is stirred for 0.5 hour, then let to crystallize at 0° C. The precipitated crystals are sucked off and the filtrate is concentrated to ½ of its volume and let to crystallize at 0° C. Both fractions (4 g+8 g) of white to brownish crystals are combined and re-crystallized from water. The yield is 7.52 g (80%).

$^1$H NMR: δ 0.99 (d, J=6.2, 3H,C$\underline{H}_3$); 2.54(dd, J=13.6 J=6.8, 1H, C$\underline{H}_2$); 2.59 (dd, J=13.6; J=6.7; 1H, C$\underline{H}_2$); 3.00(sex, J=6.4; 1H, C$\underline{H}$); 3.53(bs, N$\underline{H}_2$); 3.92(s, 3H, C$\underline{H}_3$O); 7.16(d, J=8.4; 1H, C$\underline{H}_{arom}$); 7.41(dd, J=8.4; J=2.2; 1H, C$\underline{H}_{arom}$); 7.59(d, J=2.2; 1H, C$\underline{H}_{arom}$). (CD$_3$SOCD$_3$, 30° C.)

Example 6

Comparative

A Method of Preparation of Tamsulosin (II) According to the Prior Art in Comparison with the Method with Included Steps According to the Invention 1. The Method According to the Prior Art 1.1. Chlorosulfonation in Two Steps According to U.S. Pat. No. 4,731,478 (1988)

1.2.

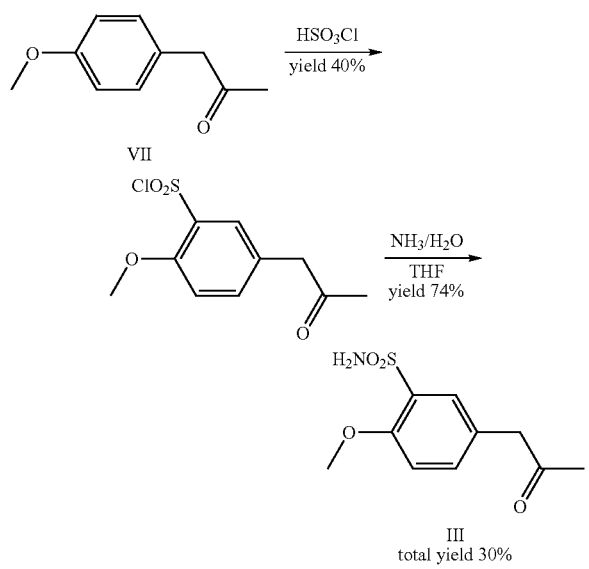

1.2. Hydrogenation on Platinum According to EP 0 257 787 (1987)

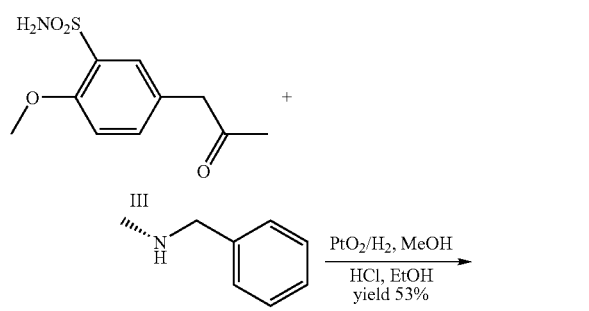

-continued

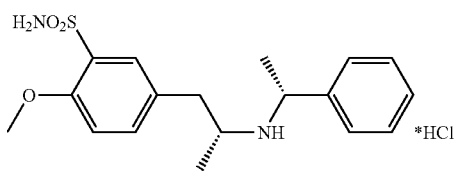

The catalyst is used in the amount of 1 g/1 mol of ketone, hydrogenation takes place in methanol under normal pressure for 20 hours. For purification to the desired optical purity (below 0.2%), the substance is purified 4× in acetone and 3× in a mixture of water and acetone.

1.3. Hydrogenation on Palladium According to EP 0 257 787

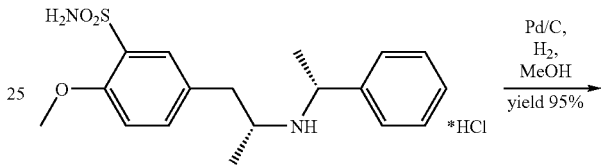

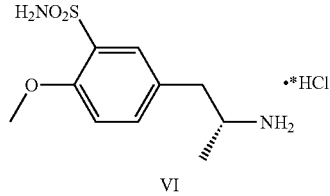

Hydrogenation in methanol under normal pressure, the catalyst is 10% palladium on carbon in the amount of 10% of the weight of the starting substance, the reaction time is not specified.

1.4. Conversion to the Base

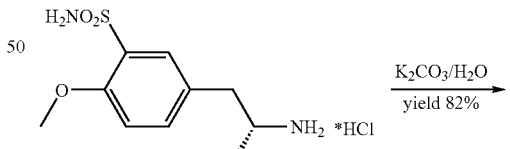

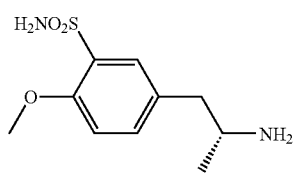

1.5. Tamsulosin

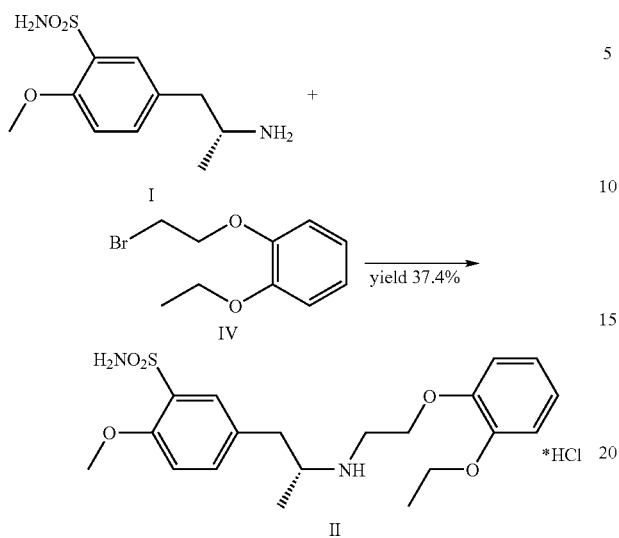

Reflux in ethanol for 16 hours, double amount of the amine used, purification by chromatography, the yield is given for the crude base, the yield of the hydrochloride is not mentioned.

2. New Synthesis According to the Invention

2.1 Hydrogenation on Platinum

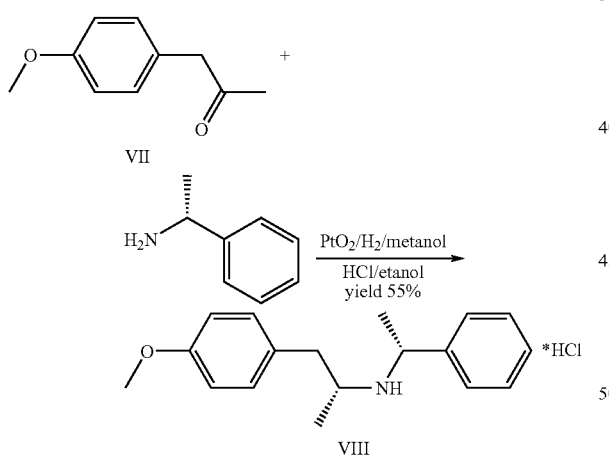

Into an autoclave are charged: 23.1 g (0.141 mol) of 4-methoxybenzylmethylketone VII, 17.2 g of R(+)-methylbenzylamine (0.142 mol), catalyst $PtO_2$ (0.05 g) and methanol (450 ml) is added. Hydrogenation is carried out under normal pressure at 60 to 62° C. for 12 hours. After the reaction mixture is processed with an ethanolic solution of HCl, intermediate VIII is obtained, which is purified by boiling in acetone. The yield is 24.62 g (57%).

Hydrogenation takes place under normal pressure for about 12 hours, the catalyst is used in the amount of 0.6 g/1 mol of the ketone. Purification in acetone is repeated 1 to 3× until the desired optical purity, whose limit has been established as maximally 0.4% of the undesired diastereoisomer.

2.2 Preparation of the Acetyl Derivative

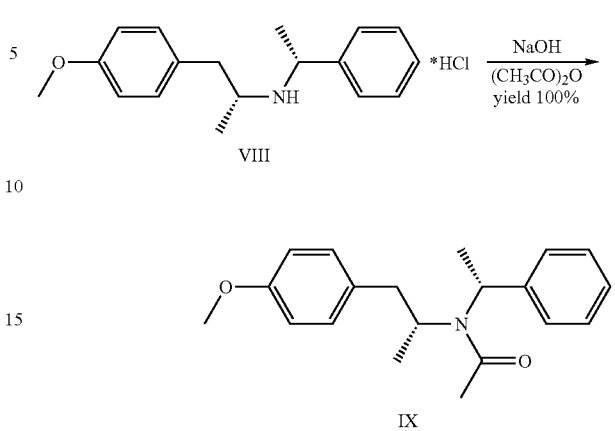

Intermediate VIII, 6377 g (20.85 mol), is converted to the base with 10% aqueous solution of NaOH (15.9 l), extracted with ethylacetate, the solvent is evaporated and the evaporation residue is heated in acetanhydride (26.57 l) at 65 to 70° C. for 6 hours. After evaporation, 6693 g (~100%) of intermediate IX were obtained.

2.3. Chlorosulfonation

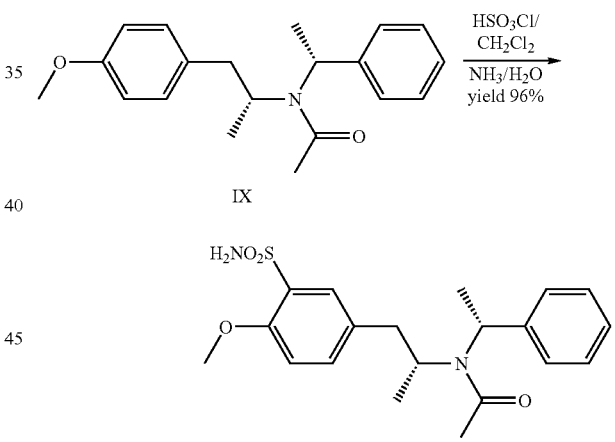

The evaporation residue 1× from the preceding step, 6690 g (~20.85 mol), is stirred in dichloromethane (13.17 l) and chlorosulfonic acid (13.75 l) is added dropwise at −5 to +2° C. After 1 hour, the reaction mixture is decomposed in a mixture of ice (65.5 kg) and 25% aqueous solution of ammonia (65.5 l). Product X is extracted with ethylacetate and the yield after evaporation is 8068 g (96.20%) of intermediate X.

The sulfochloride, resulting from the chlorosulfonation, is preferably not isolated but converted directly to sulfonamide X by decomposition of the reaction mixture in an aqueous solution of ammonia. In this manner of carrying out the reaction tetrahydrofuran as another solvent in the synthesis is avoided. The yield is unusually high for this type of reactions.

2.4. Hydrogenation on Palladium

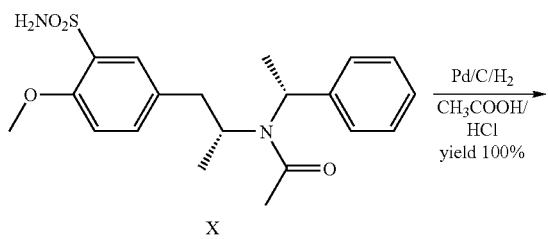

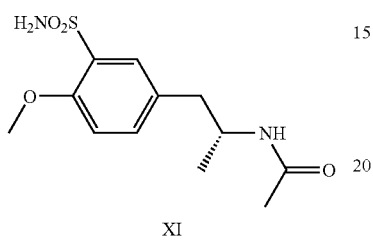

24.62 g (0.063 mol) of intermediate X is hydrogenated in an autoclave with the catalyst 3% Pd/C with 50% water content (2.5 g) in acetic acid (160 ml) with addition of diluted hydrochloric acid (1:1; 19 ml) at 80 to 85° C. and pressure of 2 MPa for 12 hours. After the reaction mixture is processed, the yield is 22.13 g (~100%) of intermediate XI.

Hydrogenation takes place at 80 to 85° C. and pressure of 2 MPa for 15 hours in acetic acid with addition of diluted hydrochloric acid. The catalyst in the amount 1/10 of the weight of the starting substance X is 3% Pd/C with 50% water content, which is significantly cheaper and safer than 10% Pd/C, which very easily burns. Yields are virtually 100%.

2.5. Deacetylation (According to U.S. Pat. No. 4,731,478, 1988)

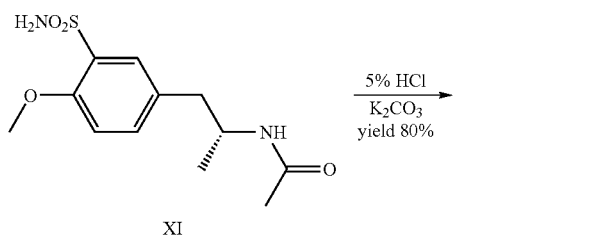

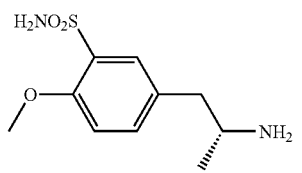

Intermediate XI (28.2 g; 0.063 mol) is refluxed in 5% aqueous HCl (660 ml) for 18 hours, after concentration product I is precipitated by addition of a saturated solution of potassium carbonate (140 ml) in two fractions (10.4 g+37.3 g). After re-crystallization from water, the yield was 17.1 g (80%).

2.6. Tamsulosin

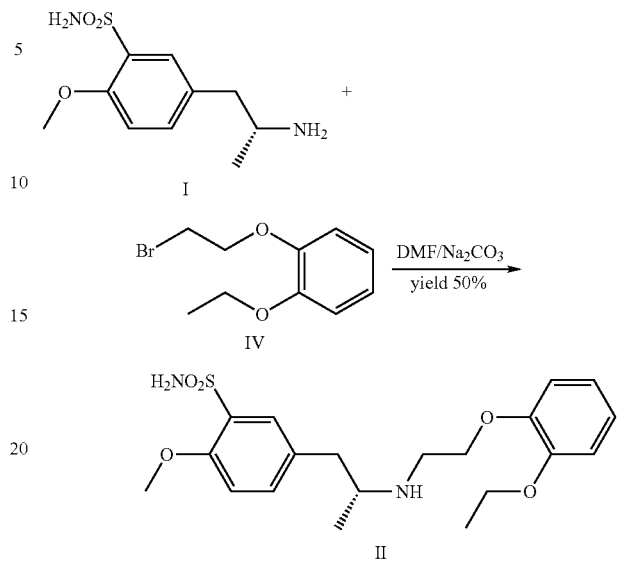

220 g (0.88 mol) of intermediate IV and 84 g (0.79 mol) of sodium carbonate and N,N-dimethylformamide (1500 ml) are added to 208 g (0.85 mol) of intermediate I. The reaction mixture is stirred at 70° C. for 5 hours. Water is added to the reaction mixture and product II is extracted with ethylacetate. The evaporation residue is stirred in ethanol and after sucking off, the yield is 173.9 g (50%) of crude base II.

The method according to CZ 291802. The yield is, for comparison, also calculated on the crude base. The reaction takes place at 60 to 70° C. for 5 hours and the product is not purified with the demanding column chromatography.

CONCLUSION

Comparison of total yields is made starting with 4-methoxyphenylacetone VII, although in EP 257787, preparation is described only starting from intermediate III.

A/The yield of (R)-(−)-5-(2-aminopropyl)-2-methoxybenzenesulfonamide I without the final condensation to tamsulosin II, i.e. reactions 1.1. through 1.4, is 12.38%; and our method—reactions 2.1. through 2.5.—yields 38.40%, i.e. it offers three times higher yield.

B/If we compare also the last step to the crude base the total yield of the synthesis of tamsulosin according to the patent EP 257787 is 4.63%, compared with our 19.20% which is a four times higher yield.

The invention claimed is:
1. A method of preparation of (R)-(−)-5-(2-aminopropyl)-2-methoxybenzenesulfonamide of formula I

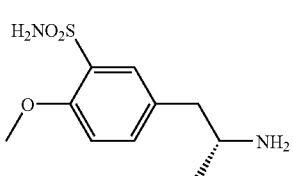

wherein
  a. a protecting group is introduced to N-[(1R)-2-(4-methoxyphenyl)-1-methylethyl]-N-[(1R)-1-phenylethyl]amine of formula VIII

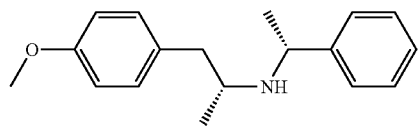

to obtain an amide of formula IX

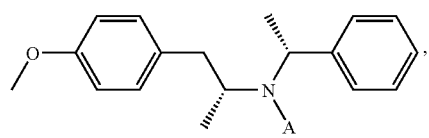

wherein A can be an acyl having 2 to 8 carbons,
  b. whereupon the amide of formula IX is chlorosulfonated and the resulting sulfochloride is converted to a sulfonamide of formula X

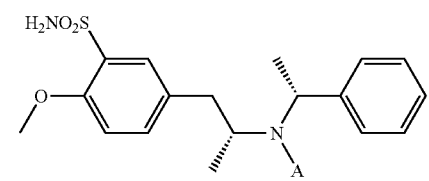

wherein A is as defined above,
  c. and the sulfonamide of formula X is hydrogenated to obtain the compound of formula I.

2. The method according to claim 1 wherein the protecting group A is an acyl.

3. The method according to claim 2 wherein acetanhydride at 50 to 100° C. is used as the acetylation agent.

4. The method according to claim 1 wherein the sulfochloride resulting from chlorosulfonation is not isolated and is directly converted to the sulfonamide with ammonia.

5. The method according to claim 4 wherein chlorosulfonation takes place in methylenechloride at −30 to +30° C.

6. The method according to claim 1 wherein hydrogenation is carried out under catalysis with palladium.

7. The method according to claim 6 wherein the catalyst is 3% Pd/C with 50% water content at a pressure of 1 to 5 MPa and a temperature of 50 to 100° C.

8. A method of preparation of (R)-(−)-5-[2-[2-(2-ethoxyphenoxy)ethylamino]propyl]-2-methoxybenzenesulfonamide of formula II

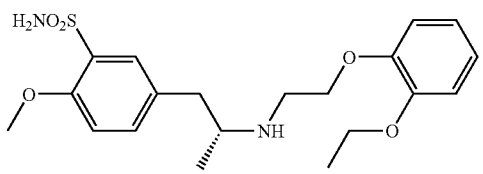

wherein the intermediate of formula I produced according to any of the preceding claims is used for the synthesis.

9. The method according to claim 8 characterized in that intermediate I is reacted with a compound of formula IV

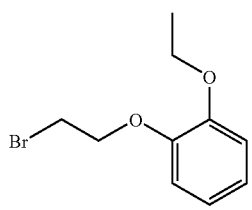

10. A sulfonamide of formula X

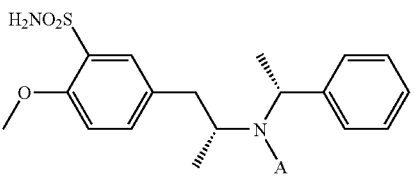

wherein A is as defined in claim 1.

11. The sulfonamide according to claim 10, wherein A is acetyl.

12. The method according to claim 2 wherein the protecting group A is acetyl.

* * * * *